(12) United States Patent
Mullaney et al.

(10) Patent No.: US 11,372,172 B2
(45) Date of Patent: Jun. 28, 2022

(54) FIBER OPTIC CONNECTOR WITH FIELD INSTALLABLE OUTER CONNECTOR HOUSING

(71) Applicant: CommScope Technologies LLC, Hickory, NC (US)

(72) Inventors: Julian S. Mullaney, Raleigh, NC (US); Eric Emmanuel Alston, Fuquay-Varina, NC (US); William Alan Carrico, Raleigh, NC (US)

(73) Assignee: CommScope Technologies LLC, Hickory, NC (US)

( * ) Notice: Subject to any disclaimer, the term of this patent is extended or adjusted under 35 U.S.C. 154(b) by 0 days.

(21) Appl. No.: 16/819,750

(22) Filed: Mar. 16, 2020

(65) Prior Publication Data

US 2020/0284991 A1    Sep. 10, 2020

Related U.S. Application Data

(63) Continuation of application No. 16/278,266, filed on Feb. 18, 2019, now Pat. No. 10,591,678, which is a
(Continued)

(51) Int. Cl.
*G02B 6/38* (2006.01)
*G02B 6/46* (2006.01)

(52) U.S. Cl.
CPC ........... *G02B 6/387* (2013.01); *G02B 6/3821* (2013.01); *G02B 6/3831* (2013.01);
(Continued)

(58) Field of Classification Search
CPC .................................................... G02B 6/387
See application file for complete search history.

(56) References Cited

U.S. PATENT DOCUMENTS

| | | |
|---|---|---|
| 4,201,444 A | 5/1980 | McCartney et al. |
| 4,217,030 A | 8/1980 | Howarth |

(Continued)

FOREIGN PATENT DOCUMENTS

| | | |
|---|---|---|
| CN | 1175002 A | 3/1998 |
| CN | 1333471 A | 1/2002 |

(Continued)

OTHER PUBLICATIONS

Fabricating with Xiameter® High Consistency Silicon Rubber, Product Guide, Silicones Simplified Xiameter® from Dow Corning, 50 pages (2009).

(Continued)

*Primary Examiner* — Charlie Y Peng
(74) *Attorney, Agent, or Firm* — Merchant & Gould P.C.

(57) ABSTRACT

An optical connector includes a first sub-assembly that is factory-installed to a first end of an optical fiber and a second sub-assembly that is field-installed to the first end of the optical fiber. The optical fiber and first sub-assembly can be routed through a structure (e.g., a building) prior to installation of the second sub-assembly. The second sub-assembly interlocks with the first sub-assembly to inhibit relative axial movement therebetween. Example first sub-assemblies include a ferrule, a hub, and a strain-relief sleeve that mount to an optical fiber. Example second sub-assemblies include a mounting block; and an outer connector housing forming a plug portion.

27 Claims, 7 Drawing Sheets

Related U.S. Application Data continuation of application No. 15/948,258, filed on Apr. 9, 2018, now Pat. No. 10,215,930, which is a continuation of application No. 15/224,069, filed on Jul. 29, 2016, now Pat. No. 9,939,591, which is a continuation of application No. 14/934,354, filed on Nov. 6, 2015, now Pat. No. 9,417,403, which is a continuation of application No. 14/091,984, filed on Nov. 27, 2013, now Pat. No. 9,182,567.

(60) Provisional application No. 61/731,838, filed on Nov. 30, 2012.

(52) U.S. Cl.
CPC ......... *G02B 6/3851* (2013.01); *G02B 6/3863* (2013.01); *G02B 6/3869* (2013.01); *G02B 6/3871* (2013.01); *G02B 6/3887* (2013.01); *G02B 6/46* (2013.01); *Y10T 29/49826* (2015.01)

(56) References Cited

U.S. PATENT DOCUMENTS

| | | |
|---|---|---|
| 4,268,115 A | 5/1981 | Slemon et al. |
| 4,327,964 A | 5/1982 | Haesly et al. |
| 4,635,875 A | 1/1987 | Apple |
| 4,691,988 A | 9/1987 | Tremblay et al. |
| 4,715,675 A | 12/1987 | Kevern et al. |
| 4,762,389 A | 8/1988 | Kaihara |
| 5,212,752 A | 5/1993 | Stephenson et al. |
| 5,216,733 A | 6/1993 | Nagase et al. |
| 5,231,685 A | 7/1993 | Hanzawa et al. |
| 5,245,683 A | 9/1993 | Belenkiy et al. |
| 5,253,315 A | 10/1993 | Fentress |
| 5,261,019 A | 11/1993 | Beard et al. |
| 5,287,425 A | 2/1994 | Chang |
| 5,452,386 A | 9/1995 | Van Woesik |
| 5,465,313 A | 11/1995 | Belenkiy et al. |
| 5,471,713 A | 12/1995 | Alter et al. |
| 5,524,159 A | 6/1996 | Turgeon et al. |
| 5,619,610 A | 4/1997 | King et al. |
| 5,637,010 A | 6/1997 | Jost et al. |
| 5,640,476 A | 6/1997 | Womack et al. |
| 5,682,451 A | 10/1997 | Lee et al. |
| 5,809,192 A | 9/1998 | Manning et al. |
| 5,862,289 A | 1/1999 | Walter et al. |
| 5,863,083 A | 1/1999 | Giebel et al. |
| 5,897,393 A | 4/1999 | Haftmann |
| 5,898,808 A | 4/1999 | Morlion et al. |
| 5,915,058 A | 6/1999 | Clairardin et al. |
| 5,946,435 A | 8/1999 | Zheng et al. |
| 5,946,436 A | 8/1999 | Takashi |
| 5,953,475 A | 9/1999 | Beier et al. |
| 6,019,520 A | 2/2000 | Lin et al. |
| 6,079,881 A | 6/2000 | Roth |
| 6,081,647 A | 6/2000 | Roth et al. |
| 6,151,432 A | 11/2000 | Nakajima et al. |
| 6,154,597 A | 11/2000 | Roth |
| 6,245,999 B1 | 6/2001 | Costigan et al. |
| 6,287,018 B1 | 9/2001 | Andrews et al. |
| 6,296,399 B1 | 10/2001 | Halbach et al. |
| 6,325,547 B1 | 12/2001 | Cammons et al. |
| 6,396,993 B1 | 5/2002 | Giebel et al. |
| 6,398,422 B1 | 6/2002 | Szilagyi et al. |
| 6,419,399 B1 | 7/2002 | Loder et al. |
| 6,428,215 B1 | 8/2002 | Nault |
| 6,429,373 B1 | 8/2002 | Scrimpshire et al. |
| 6,540,410 B2 | 4/2003 | Childers et al. |
| 6,550,978 B2 | 4/2003 | De Marchi |
| 6,579,014 B2 | 6/2003 | Melton et al. |
| 6,648,520 B2 | 11/2003 | McDonald et al. |
| 6,672,774 B2 | 1/2004 | Theuerkorn et al. |
| 6,695,489 B2 | 2/2004 | Nault |
| 6,811,321 B1 | 11/2004 | Schmalzigaug et al. |
| 6,899,467 B2 | 5/2005 | McDonald et al. |
| 6,902,140 B1 | 6/2005 | Huang |
| 6,913,392 B2 | 7/2005 | Grzegorzewska et al. |
| 6,935,789 B2 | 8/2005 | Gross, III et al. |
| 6,945,704 B2 | 9/2005 | Yamaguchi |
| 6,960,025 B2 | 11/2005 | Gurreri |
| 7,090,406 B2 | 8/2006 | Melton et al. |
| 7,147,384 B2 | 12/2006 | Hardcastle et al. |
| 7,198,409 B2 | 4/2007 | Smith et al. |
| 7,204,016 B2 | 4/2007 | Roth et al. |
| 7,204,644 B2 | 4/2007 | Barnes et al. |
| 7,226,215 B2 | 6/2007 | Bareel et al. |
| 7,281,859 B2 | 10/2007 | Mudd et al. |
| 7,344,317 B2 | 3/2008 | Krowiak et al. |
| 7,357,579 B2 | 4/2008 | Feldner |
| 7,369,738 B2 | 5/2008 | Larson et al. |
| 7,510,335 B1 | 3/2009 | Su et al. |
| 7,530,745 B2 | 5/2009 | Holmquist |
| 7,572,065 B2 | 8/2009 | Lu et al. |
| 7,574,095 B2 | 8/2009 | Lock et al. |
| 7,614,797 B2 | 11/2009 | Lu et al. |
| 7,614,799 B2 | 11/2009 | Bradley et al. |
| 7,676,132 B1 | 3/2010 | Mandry et al. |
| 7,712,974 B2 | 5/2010 | Yazaki et al. |
| 7,744,288 B2 | 6/2010 | Lu et al. |
| 7,775,726 B2 | 8/2010 | Pepin et al. |
| 7,785,015 B2 | 8/2010 | Melton et al. |
| 7,806,599 B2 | 10/2010 | Margolin et al. |
| 7,838,775 B2 | 11/2010 | Montena |
| 8,311,378 B2 | 11/2012 | Niyama et al. |
| 8,391,664 B2 | 3/2013 | Kowalczyk et al. |
| 8,393,803 B2 | 3/2013 | Hogue |
| 8,439,577 B2 | 5/2013 | Jenkins |
| 8,443,488 B2 | 5/2013 | Zhang |
| 8,480,312 B2 | 7/2013 | Smith et al. |
| 8,548,293 B2 | 10/2013 | Kachmar |
| 8,577,199 B2 | 11/2013 | Pierce et al. |
| 8,647,140 B2 | 2/2014 | Annecke |
| 8,753,022 B2 | 6/2014 | Schroeder et al. |
| 8,821,180 B2 | 9/2014 | Blakborn et al. |
| 9,106,003 B2 | 8/2015 | Anderson et al. |
| 9,130,303 B2 | 9/2015 | Anderson et al. |
| 9,182,567 B2 | 11/2015 | Mullaney |
| 9,216,530 B2 | 12/2015 | Vaccaro |
| 9,229,173 B2 | 1/2016 | Yamauchi et al. |
| 9,239,441 B2 | 1/2016 | Melton et al. |
| 9,268,102 B2 | 2/2016 | Daems et al. |
| 9,285,559 B1 | 3/2016 | Stockton et al. |
| 9,297,976 B2 | 3/2016 | Hill et al. |
| 9,417,403 B2 | 8/2016 | Mullaney et al. |
| 9,470,847 B2 | 10/2016 | Grinderslev |
| 9,557,496 B2 | 1/2017 | Irwin et al. |
| 9,684,138 B2 | 6/2017 | Lu |
| 9,739,971 B2 | 8/2017 | Eberle, Jr. et al. |
| 9,804,342 B2 | 10/2017 | Little et al. |
| 9,829,649 B2 | 11/2017 | Liu et al. |
| 9,910,224 B2 | 3/2018 | Liu et al. |
| 9,939,591 B2 | 4/2018 | Mullaney et al. |
| 9,971,104 B2 | 5/2018 | Tong et al. |
| 10,018,797 B2 | 7/2018 | Cheng et al. |
| 10,067,301 B2 | 9/2018 | Murray et al. |
| 10,073,224 B2 | 9/2018 | Tong et al. |
| 10,215,930 B2 | 2/2019 | Mullaney et al. |
| 10,281,649 B2 | 5/2019 | Nhep et al. |
| 10,466,425 B2 | 11/2019 | Liu et al. |
| 10,473,867 B2 | 11/2019 | Tong et al. |
| 10,591,678 B2 | 3/2020 | Mullaney et al. |
| 10,613,278 B2 | 4/2020 | Kempeneers |
| 10,620,385 B2 | 4/2020 | Nhep et al. |
| 10,641,970 B2 | 5/2020 | Ott et al. |
| 10,698,166 B2 | 6/2020 | Liu et al. |
| 10,895,698 B2 | 1/2021 | Nhep et al. |
| 10,976,500 B2 | 4/2021 | Ott et al. |
| 11,002,917 B2 | 5/2021 | Liu et al. |
| 11,119,283 B2 | 9/2021 | Tong et al. |
| 2001/0012428 A1 | 8/2001 | Nakajima et al. |
| 2001/0014197 A1 | 8/2001 | De Marchi |
| 2002/0076165 A1 | 6/2002 | Childers et al. |
| 2002/0106163 A1 | 8/2002 | Cairns |

(56) References Cited

U.S. PATENT DOCUMENTS

| | | |
|---|---|---|
| 2002/0139966 A1 | 10/2002 | Griffioen et al. |
| 2002/0186934 A1 | 12/2002 | Hug et al. |
| 2003/0063868 A1 | 4/2003 | Fentress |
| 2003/0077045 A1 | 4/2003 | Fleenor et al. |
| 2003/0215191 A1 | 11/2003 | Taira et al. |
| 2003/0231839 A1 | 12/2003 | Chen et al. |
| 2004/0023598 A1 | 2/2004 | Zimmel et al. |
| 2004/0076389 A1 | 4/2004 | Ozaki |
| 2004/0101254 A1 | 5/2004 | Erdman et al. |
| 2004/0105625 A1 | 6/2004 | Ueda et al. |
| 2004/0117981 A1 | 6/2004 | Roth et al. |
| 2004/0165832 A1 | 8/2004 | Bates, III et al. |
| 2004/0223699 A1 * | 11/2004 | Melton ............... G02B 6/387 385/53 |
| 2005/0084215 A1 | 4/2005 | Grzegorzewska et al. |
| 2005/0135755 A1 | 6/2005 | Kiani et al. |
| 2006/0093300 A1 | 5/2006 | Marrs et al. |
| 2006/0115219 A1 | 6/2006 | Mudd et al. |
| 2007/0025665 A1 | 2/2007 | Dean, Jr. et al. |
| 2007/0172173 A1 | 7/2007 | Adomeit et al. |
| 2007/0263960 A1 | 11/2007 | Lock et al. |
| 2007/0284146 A1 | 12/2007 | Dower et al. |
| 2008/0011990 A1 | 1/2008 | Kostet et al. |
| 2008/0013891 A1 | 1/2008 | Nishioka et al. |
| 2008/0089650 A1 | 4/2008 | Legler et al. |
| 2008/0175546 A1 | 7/2008 | Lu et al. |
| 2008/0226234 A1 | 9/2008 | Droege |
| 2008/0226236 A1 | 9/2008 | Pepin et al. |
| 2008/0273855 A1 | 11/2008 | Bradley et al. |
| 2009/0148101 A1 | 6/2009 | Lu et al. |
| 2009/0148109 A1 | 6/2009 | Takahashi et al. |
| 2009/0185779 A1 | 7/2009 | Gurreri et al. |
| 2010/0202748 A1 | 8/2010 | Pierce et al. |
| 2011/0002586 A1 | 1/2011 | Nhep |
| 2011/0097044 A1 | 4/2011 | Saito et al. |
| 2011/0170829 A1 | 7/2011 | Bradley |
| 2011/0176785 A1 | 7/2011 | Kowalczyk et al. |
| 2012/0027355 A1 | 2/2012 | LeBlanc et al. |
| 2012/0170896 A1 | 7/2012 | Skluzacek et al. |
| 2012/0243831 A1 | 9/2012 | Chen |
| 2012/0257859 A1 | 10/2012 | Nhep |
| 2013/0058615 A1 | 3/2013 | Matthew et al. |
| 2013/0077928 A1 | 3/2013 | Hsing |
| 2013/0094828 A1 | 4/2013 | Loeffelholz et al. |
| 2013/0101258 A1 | 4/2013 | Hikosaka et al. |
| 2013/0177283 A1 | 7/2013 | Theuerkorn et al. |
| 2013/0322826 A1 | 12/2013 | Henke et al. |
| 2014/0023326 A1 | 1/2014 | Anderson et al. |
| 2014/0050446 A1 | 2/2014 | Chang et al. |
| 2014/0086534 A1 | 3/2014 | Lu et al. |
| 2014/0133808 A1 | 5/2014 | Hill et al. |
| 2014/0153878 A1 | 6/2014 | Mullaney |
| 2014/0219621 A1 | 8/2014 | Barnette, Jr. et al. |
| 2014/0235091 A1 | 8/2014 | Wang et al. |
| 2014/0295700 A1 | 10/2014 | Natoli et al. |
| 2015/0017827 A1 | 1/2015 | Vaccaro |
| 2015/0136439 A1 | 5/2015 | Vaccaro |
| 2015/0268434 A1 | 9/2015 | Barnette, Jr. et al. |
| 2015/0338582 A1 | 11/2015 | Halls et al. |
| 2016/0187590 A1 | 6/2016 | Lu |
| 2016/0306122 A1 | 10/2016 | Tong et al. |
| 2016/0349458 A1 | 12/2016 | Murray et al. |
| 2016/0356963 A1 | 12/2016 | Liu et al. |
| 2016/0356964 A1 | 12/2016 | Liu et al. |
| 2017/0131509 A1 | 5/2017 | Xiao et al. |
| 2018/0106972 A1 | 4/2018 | Liu et al. |
| 2018/0224608 A1 | 8/2018 | Liu et al. |
| 2018/0348447 A1 | 12/2018 | Nhep et al. |
| 2020/0088951 A1 | 3/2020 | Liu et al. |
| 2020/0355876 A1 | 11/2020 | Liu et al. |
| 2021/0215888 A1 | 7/2021 | Nhep et al. |
| 2021/0286137 A1 | 9/2021 | Ott et al. |
| 2021/0333478 A1 | 10/2021 | Liu et al. |

FOREIGN PATENT DOCUMENTS

| | | | |
|---|---|---|---|
| CN | 1910488 A | 2/2007 | |
| CN | 101084460 A | 12/2007 | |
| CN | 101084461 A | 12/2007 | |
| CN | 101346653 A | 1/2009 | |
| CN | 101641627 A | 2/2010 | |
| CN | 201527493 U | 7/2010 | |
| CN | 201926781 U | 8/2011 | |
| CN | 102360104 A | 2/2012 | |
| CN | 102460259 A | 5/2012 | |
| CN | 202583527 U | 12/2012 | |
| CN | 202815276 U | 3/2013 | |
| CN | 202956505 U | 5/2013 | |
| CN | 102313934 | 7/2013 | |
| CN | 203054267 U | 7/2013 | |
| CN | 103353635 A | 10/2013 | |
| CN | 103718392 A * | 4/2014 | ........... H01R 13/639 |
| CN | 203688854 U | 7/2014 | |
| CN | 203786340 U | 8/2014 | |
| CN | 203825243 U | 9/2014 | |
| CN | 105093420 A | 11/2015 | |
| CN | 105093421 A | 11/2015 | |
| EP | 0 330 399 A1 | 8/1989 | |
| EP | 0 429 398 A2 | 5/1991 | |
| EP | 2128675 | 12/2009 | |
| EP | 2 355 286 A1 | 8/2011 | |
| EP | 2 482 109 A2 | 8/2012 | |
| EP | 2 031 779 B1 | 1/2013 | |
| GB | 2 509 532 A | 7/2014 | |
| JP | 2001-147344 A | 5/2001 | |
| JP | 2004-126371 A | 4/2004 | |
| JP | 2007-165235 A | 6/2007 | |
| JP | 2008-152266 A | 7/2008 | |
| WO | WO-0013052 A1 * | 3/2000 | ........... G02B 6/3801 |
| WO | 01/40839 A1 | 6/2001 | |
| WO | 02/052310 | 7/2002 | |
| WO | 2006/069092 A2 | 6/2006 | |
| WO | 2006/069093 A1 | 6/2006 | |
| WO | 2008/091720 A1 | 7/2008 | |
| WO | 2010/118031 A1 | 10/2010 | |
| WO | 2011/092084 A2 | 8/2011 | |
| WO | 2012/037727 A1 | 3/2012 | |
| WO | 2012/125836 A2 | 9/2012 | |
| WO | 2013/077969 A1 | 5/2013 | |
| WO | 2013/126429 A2 | 8/2013 | |
| WO | 2015/028433 A1 | 3/2015 | |
| WO | 2015/144883 A1 | 10/2015 | |
| WO | 2017/106507 A1 | 6/2017 | |
| WO | 2017/106514 A1 | 6/2017 | |

OTHER PUBLICATIONS

Xiameter® brand High Consistency Rubber (HCR) Bases—Asia (Excluding Japan) Selection Guide, Silicones Simplified Xiameter® from Dow Corning, 6 pages (2011).

European Search Report for Application No. 13858527.8 dated Jun. 21, 2016.

International Search Report and Written Opinion for PCT/US2013/072018 dated Mar. 25, 2014.

\* cited by examiner

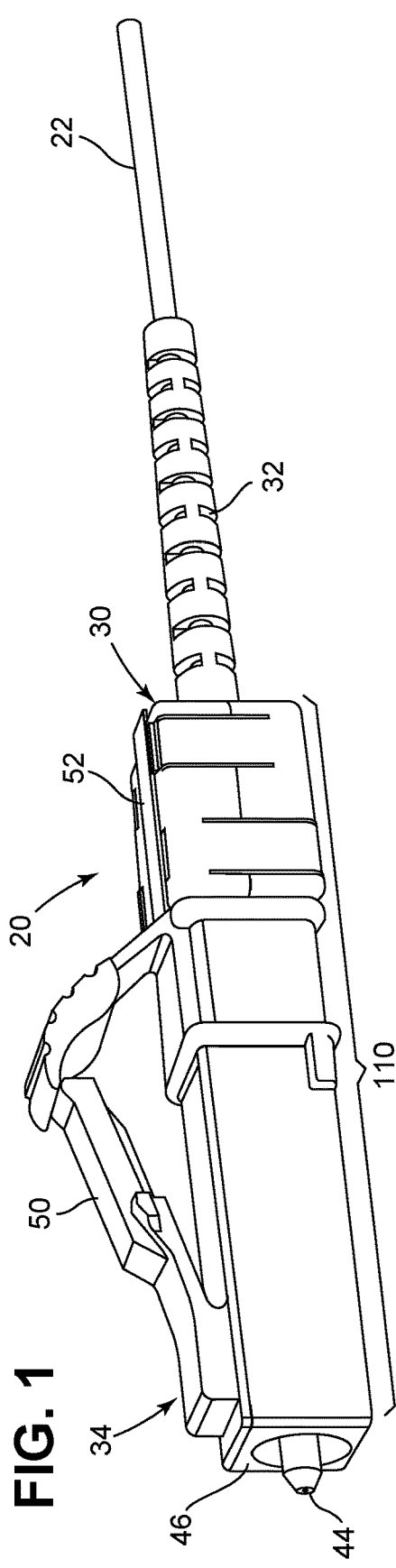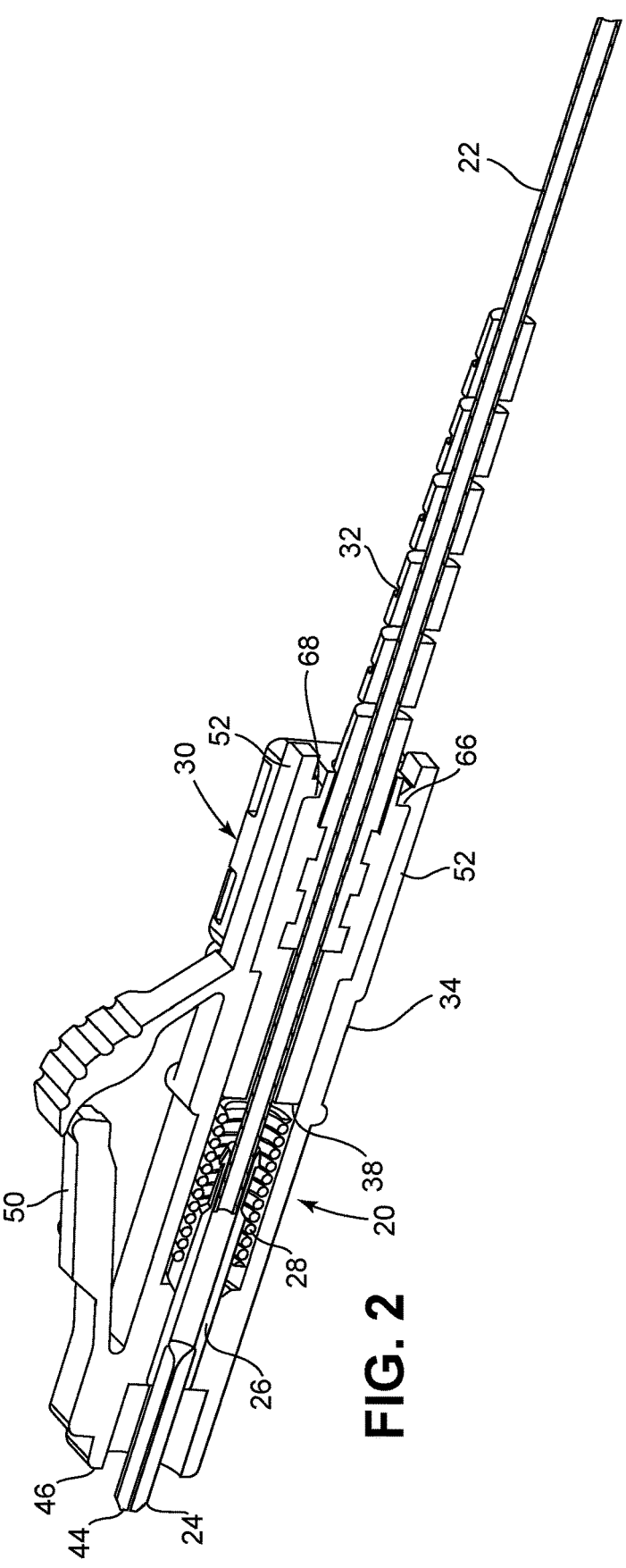

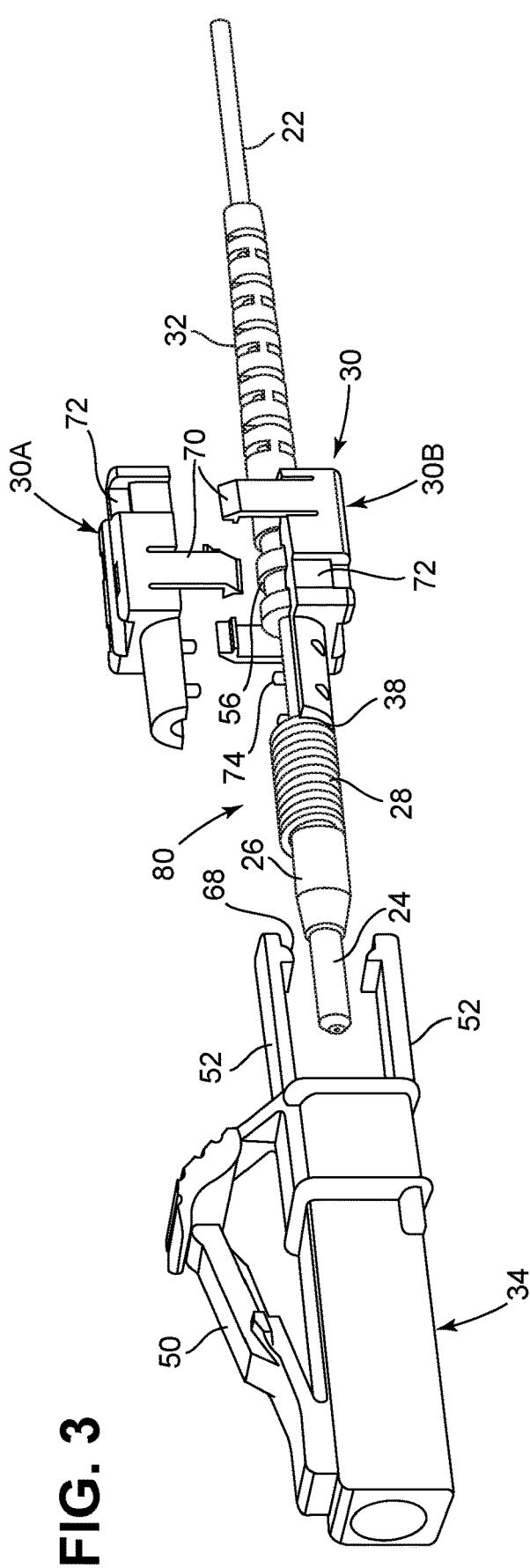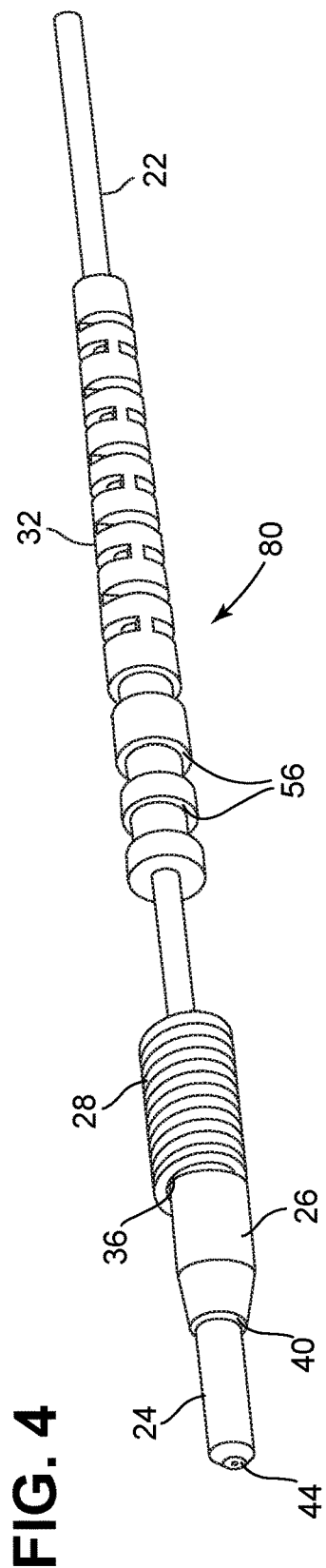

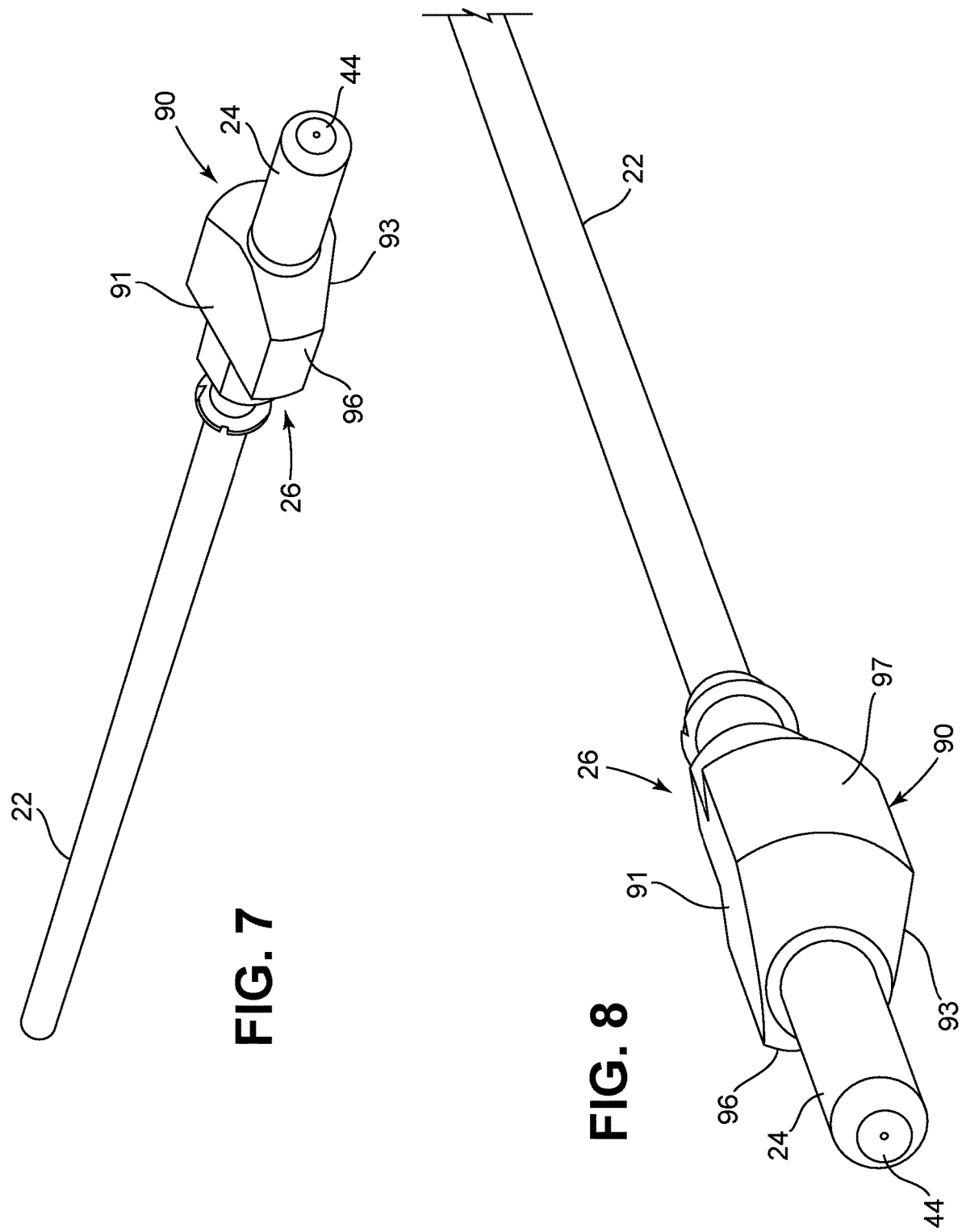

FIBER OPTIC CONNECTOR WITH FIELD INSTALLABLE OUTER CONNECTOR HOUSING

CROSS-REFERENCE TO RELATED APPLICATIONS

This application is a continuation of application Ser. No. 16/278,266, filed Feb. 18, 2019, now U.S. Pat. No. 10,591,678, which is a continuation of application Ser. No. 15/948,258, filed Apr. 9, 2018, now U.S. Pat. No. 10,215,930, which is a continuation of application Ser. No. 15/224,069, filed Jul. 29, 2016, now U.S. Pat. No. 9,939,591, which is a continuation of application Ser. No. 14/934,354, filed Nov. 6, 2015, now U.S. Pat. No. 9,417,403, which is a continuation of application Ser. No. 14/091,984, filed Nov. 27, 2013, now U.S. Pat. No. 9,182,567, which application claims the benefit of provisional application Ser. No. 61/731,838, filed Nov. 30, 2012, which applications are incorporated herein by reference in their entirety.

TECHNICAL FIELD

The present disclosure relates generally to devices used in optical fiber communication systems. More particularly, the present disclosure relates to fiber optic connectors used in optical fiber communication systems.

BACKGROUND

Fiber optic communication systems are becoming prevalent in part because service providers want to deliver high bandwidth communication capabilities (e.g., data invoice) to customers. Fiber optic communication systems employ a network of fiber optic cables to transmit large volumes of data invoice signals over relatively long distances. Optical fiber connectors are an important part of most fiber optic communication systems. Fiber optic connectors allow two optical fibers to be quickly, optically connected without requiring a splice. Fiber optic connectors can be used to optically interconnect two lengths of optical fiber. Optical fiber connectors can also be used to interconnect lengths of optical fiber to passive and active equipment.

A typical fiber optic connector includes a ferrule assembly supported at a distal end of a connector housing. A spring may be used to bias the ferrule assembly in a distal direction relative to the connector housing. The ferrule functions to support an end portion of at least one optical fiber. In the case of a multi-fiber ferrule, the ends of multiple fibers are supported. The ferrule has a distal end faced at which a polished end of the optical fiber is located. When two fiber optic connectors are interconnected, the distal end faces of the ferrules abut one another. Often, the ferrules are biased together by at least one spring. With the fiber optic connectors connected, their respective optical fibers are coaxially aligned such that the end faces of the optical fibers directly oppose one another. In this way, an optical signal can be transmitted from optical fiber to optical fiber through the aligned end faces of the optical fibers. For many fiber optic connector styles, alignment between two fiber optic connectors is provided through the use of an intermediate fiber optic adapter.

SUMMARY

One aspect of the present disclosure relates to a fiber optic connector having a field installable connector housing assembly. Another aspect of the present disclosure relates to a fiber optic connector system that facilitates installing optical fiber in ducts or other small conduits often found in buildings such a multiple dwelling units.

A further aspect of the present disclosure relates to a fiber optic connection system where a ferrule is mounted at the end of an optical fiber (e.g., at a factory or other manufacturing center), and a connector housing is field installed at the end of the optical fiber after the optical fiber has been installed at a desired location. For example, the optical fiber can be installed within a conduit, duct or other structure within a building before the connector housing is installed at the end of the optical fiber over the ferrule. In certain examples, a spring and a strain relief boot can be factory installed on the optical fiber. In certain examples, the optical fiber can include a protective buffer layer such as a 900 micron loose or tight buffer tube/jacket. In certain examples, the optical fiber can be incorporated within a cable having an outer jacket and a strength layer (e.g., an aramid yarn strength layer or other layer suitable for providing tensile reinforcement to the optical fiber) positioned between the optical fiber and the outer jacket. In certain examples, the fiber optic cable can have an outer diameter less than 1.5 millimeters or less than 1.4 millimeters or less than 1.3 millimeters, or less than or equal to 1.2 millimeters.

A variety of additional aspects will be set forth in the description that follows. The aspects relate to individual features and to combinations of features. It is to be understood that both the foregoing general description and the following detailed description are exemplary and explanatory only and are not restrictive of the broad inventive concepts upon which the examples disclosed herein are based.

BRIEF DESCRIPTION OF THE DRAWINGS

FIG. 1 is a perspective view of a fiber optic connector in accordance with the principles of the present disclosure;

FIG. 2 is a cross-sectional view of the fiber optic connector of FIG. 1 that bisects the fiber optic connector of FIG. 1 along a vertical plane;

FIG. 3 is an exploded view of the fiber optic connector of FIG. 1;

FIG. 4 is a perspective view of a factory-installed sub-assembly of the fiber optic connector of FIG. 1;

FIG. 7 is a perspective view of a ferrule assembly of the factory installed sub assembly of FIG. 4;

FIG. 8 is another perspective view of the ferrule assembly of FIG. 7;

DETAILED DESCRIPTION

Figure 5:
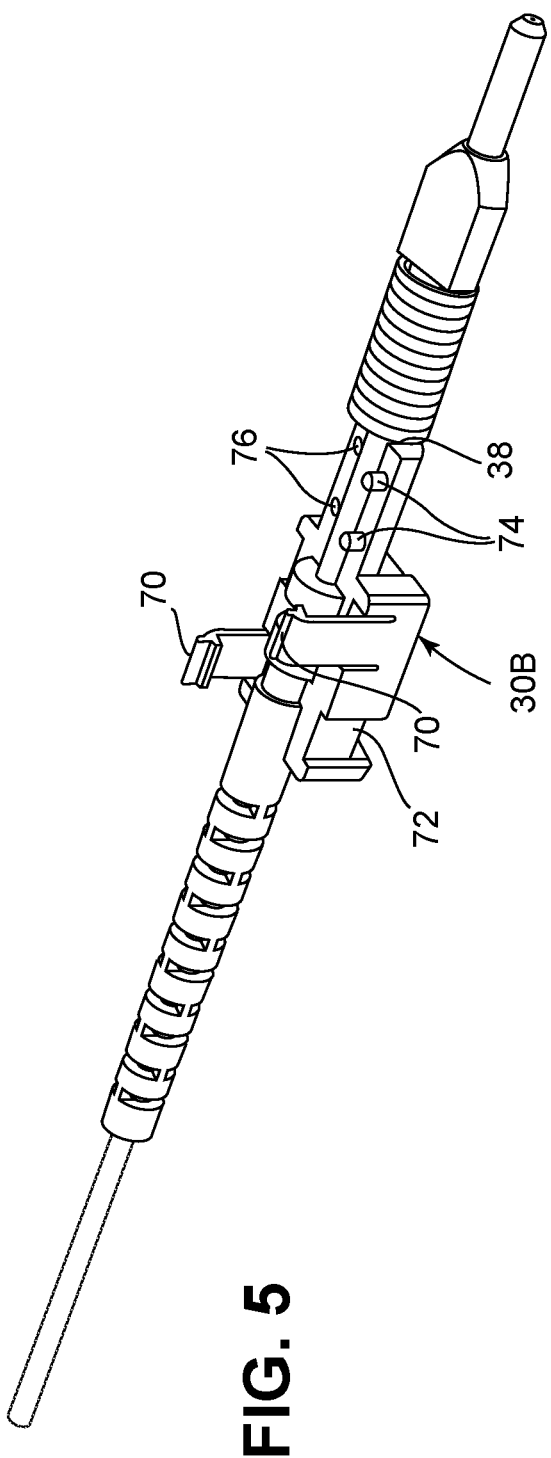
FIG. 5 illustrates a first step for installing a field installable connector housing assembly on the factory installed sub assembly of FIG. 4.

FIG. 1-3 illustrate a fiber optic connector 20 in accordance with the principles of the present disclosure. The fiber optic connector 20 is shown installed on an optical fiber 22. As shown at FIG. 3, the fiber optic connector 20 includes a ferrule 24 in which an end portion of the optical fiber 22 is supported, a ferrule hub 26 supporting the ferrule 24, a spring 28, a mounting block 30, a flexible, strain-relief sleeve 32 (e.g., a boot) that provides bend radius protection to the optical fiber 22 and a main connector housing 34. The spring 28 is captured between a backside 36 of the ferrule hub 26 and a front spring stop 38 of the mounting block 30. The mounting block 30 can interlock with the strain relief sleeve 32 to inhibit relative axial movement between the mounting block 30 and the strain relief sleeve 32.

Figure 15:
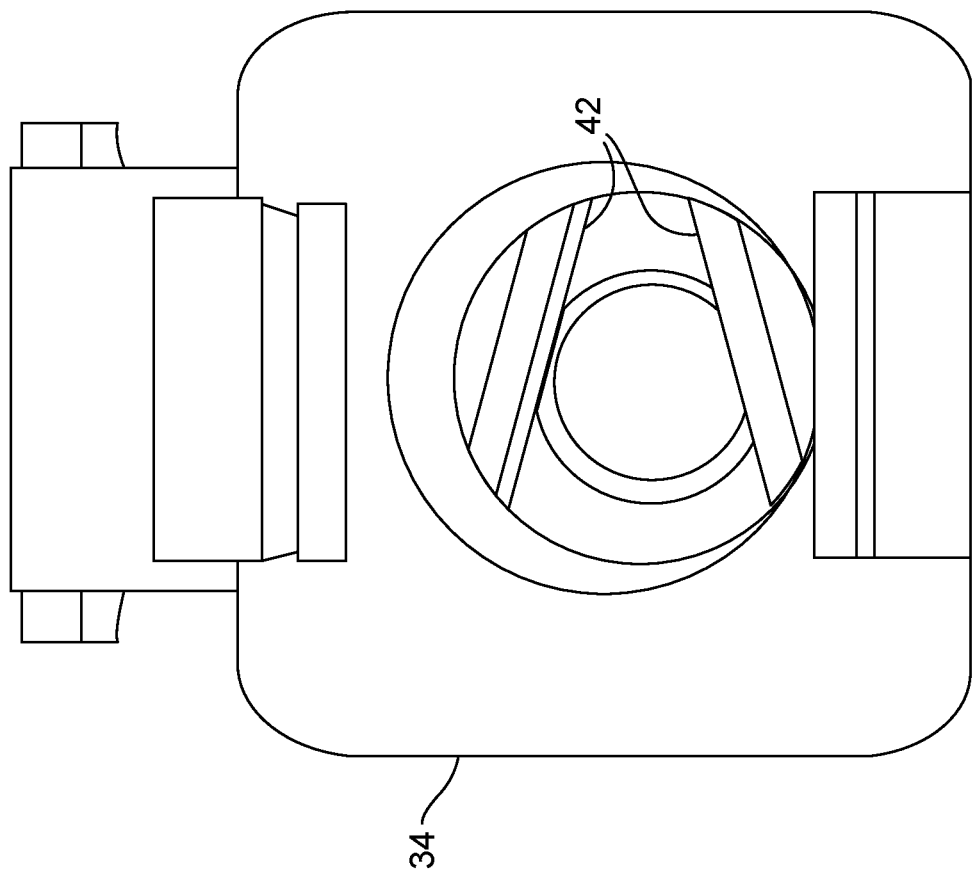
FIG. 15 is a rear view of a main connector housing of the fiber optic connector of FIG. 1.
Figure 10:
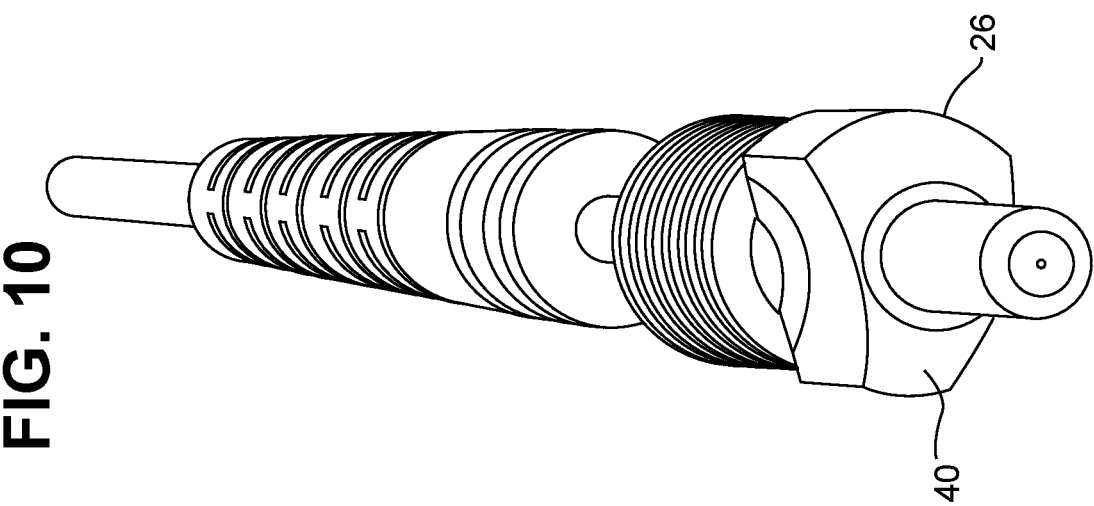
FIG. 10 is still another perspective view of the ferrule assembly of FIG. 7.
Figure 11:
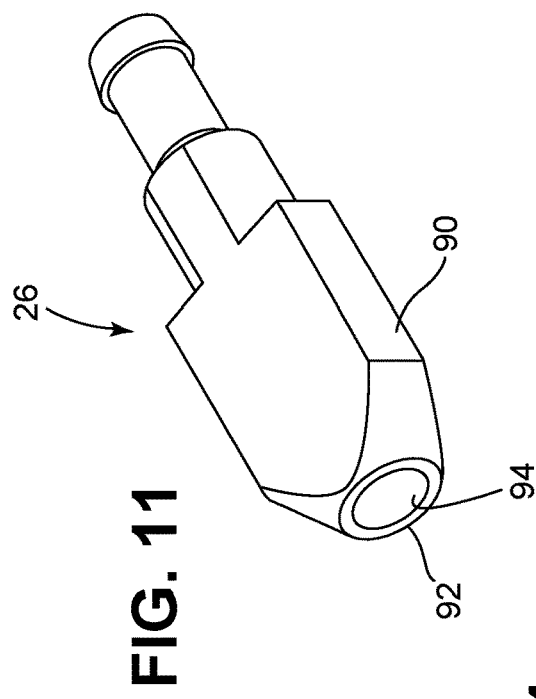
FIG. 11 is a perspective view of a ferrule hub of the ferrule assembly of FIG. 7.

The main connector housing 34 forms a front plug portion of the fiber optic connector 20 and is adapted to receive the ferrule 24, the ferrule hub 26, the spring 28 and the front spring stop 38 of the mounting block 30 (see FIG. 2). In certain examples, a keyed relationship is defined between the ferrule hub 26 and the interior of the main connector housing 34 such that the ferrule hub 26 can be inserted into the interior of the main connector housing 34 at only one predetermined rotational orientation (see FIGS. 14 and 15). A front side 40 of the ferrule hub 26 can abut against a shoulder 42 (see FIG. 15) within the main connector housing 34 to stop forward movement of the ferrule hub 26 within the main connector housing 34. The main connector housing 34 can latch or otherwise connect to the mounting block 34 such that the ferrule hub 26 and the spring 28 are captured between the main connector housing 34 and the mounting block 30 and thereby retained within the main connector housing 34 (see FIG. 2).

In certain examples, the spring 28 biases the ferrule hub 26 and the ferrule 24 in a forward direction relative to the main connector housing in 34. In certain examples, a front end face 44 of the ferrule 24 is accessible at a front end 46 of the main connector housing 34. A polished end face of the optical fiber 22 can be located at the front end face 44 of the ferrule 24. In certain examples, the front end face 44 can be angled relative to a longitudinal axis of the optical fiber 22. In other examples, front end face 44 can be perpendicular relative to the longitudinal axis of the optical fiber 22.

In certain examples, the optical fiber 22 includes a core, a cladding layer surrounding the core, one or more coating layers surrounding the cladding layer, and a buffer layer surrounding the one or more coating layers. In certain examples, the core can have an outer diameter in the range of 8-12 microns, the cladding can have an outer diameter in the range of 120-130 microns, the one or more coatings can have an outer diameter in the range of 240-260 microns, and the outer buffer layer can have an outer diameter in the range of 800-1,000 microns. In certain examples, the outer buffer layer can be a loose or tight buffer tube having an outer diameter of about 900 microns. In certain examples, only the core and the cladding of the optical fiber 22 are supported within the ferrule 24.

It will also be appreciated that the core and the cladding can be constructed of a material suitable for conveying an optical signal such a glass (e.g., a silica-based material). The cladding layer can have an index of refraction that is less than the index of refraction of the core. This difference between the index of refraction of the cladding layer and the index of refraction of the core allows an optical signal that is transmitted through the optical fiber to be confined to the core. In certain examples, the optical fiber is a bend insensitive fiber having multiple cladding layers separated by one or more trench layers. The one or more coating layers typically have a polymeric construction such as acrylate.

In certain examples, the optical fiber is incorporated into a fiber optic cable having a strength layer (e.g., a layer of aramid yarn) surrounded by an outer jacket. In certain embodiments, the buffer layer is eliminated and the strength layer directly surrounds the coating layer of the optical fiber. In certain examples, the fiber optic cable has an outer diameter less than 1.5 millimeters, or less than 1.4 millimeters, or less than 1.3 millimeters, or less than or equal to 1.2 millimeters. For example, some such optical fibers are disclosed in U.S. application Ser. No. 12/473,931, filed May 28, 2009, and titled "FIBER OPTIC CABLE," the disclosure of which is hereby incorporated herein by reference.

The main connector housing 34 of the fiber optic connector 20 forms a plug portion of the fiber optic connector 20 that is configured to fit within a corresponding fiber optic adapter. In the depicted embodiment, the main connector housing 34 is an LC-type connector housing configured to fit within an LC-type fiber optic adapter. The main connector housing 34 includes a front latch 50 for securing the main connector housing 34 within the fiber optic adapter. The main connector housing 34 also includes rear latches 52 (FIG. 3) that latch to the mounting block 34 for providing a snap-fit connection between the main connector housing 34 and the mounting block 30 (see FIG. 2). Once the main connector housing 34 and the mounting block 30 are latched together, relative axial movement between the main connector housing 34 and the mounting block 30 along the longitudinal axis of the optical fiber 22 is limited or prevented. In certain examples, the rear latches 52 can be flexed apart to disengage the main connector housing 34 from the mounting block 30 for repair, re-assembly, cleaning, or other reasons. In other examples, the main connector housing 34 can correspond to other connector types, such as SC-type connectors, ST-type connectors, FC-type connectors, or other types of connectors.

The strain relief sleeve 32 is elongated and has a central opening for receiving the optical fiber 22. In certain examples, the strain relief sleeve 32 has a polymeric construction and is flexible. In certain examples, the strain relief sleeve 32 has a tapered construction that reduces in cross-sectional size as the strain relief sleeve 32 extends rearwardly from the mounting block 30. In certain examples, the strain relief sleeve 32 can have a segmented construction that enhances flexibility (see FIG. 2). As shown at FIG. 3, a forward end portion of the strain relief sleeve 32 defines two axially spaced apart circumferential grooves 56 that receive corresponding circumferential ribs defined within the mounting block 30 (see FIG. 3) to provide a mechanical interlock between the strain relief sleeve 32 and the mounting block 30. The mechanical interlock inhibits or prevents relative axial movement between the strain relief sleeve 32 and the mounting block 30. In this way, the strain relief sleeve 32 is locked in place relative to the mounting block 30 when the mounting block 30 is mounted over the strain relief sleeve 32.

Figure 6:
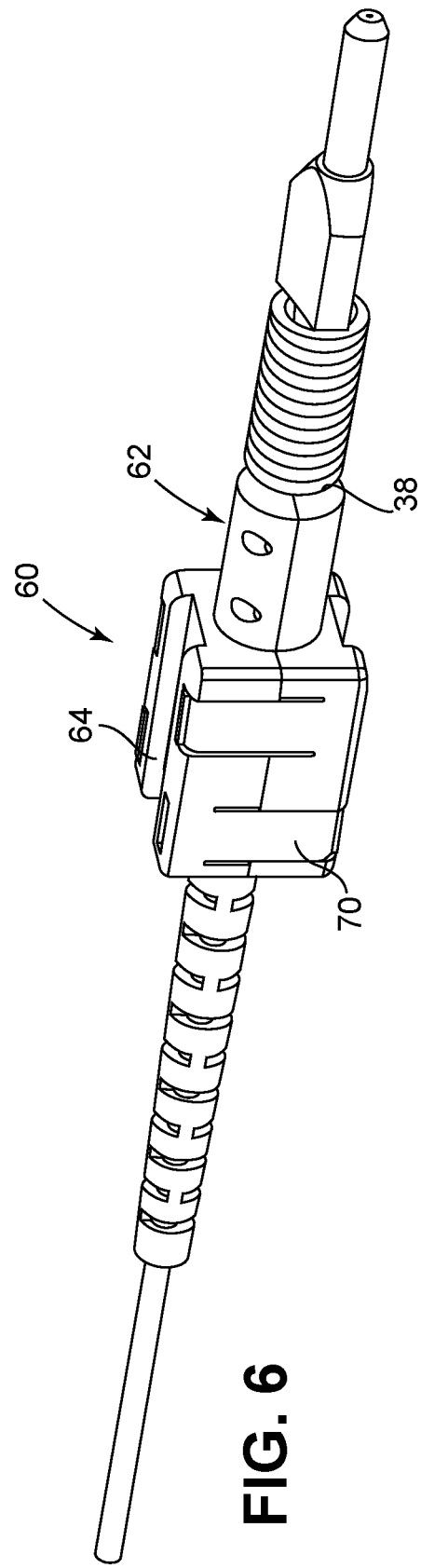
FIG. 6 illustrates a second step for installing the field installable connector housing assembly on the factory installed sub assembly of FIG. 4.
Figure 9:
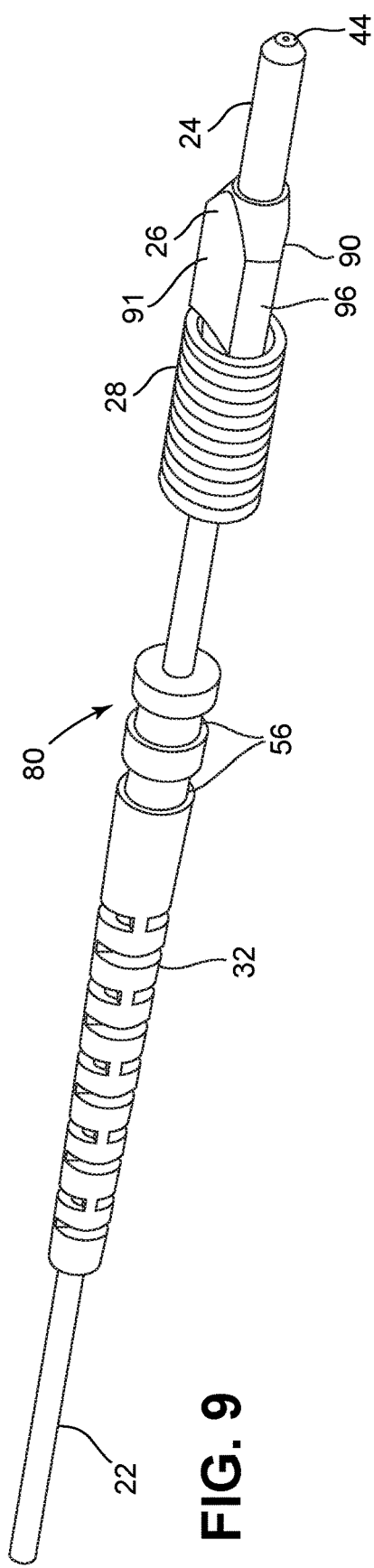
FIG. 9 is a further perspective view of the ferrule assembly of FIG. 7.

Referring to FIG. 6, the mounting block 30 has a generally rectangular main body 60 and a front extension 62 that projects forwardly from the main body 60. A front end of the front extension 62 forms the front spring stop 38. The main body 60 includes top and bottom axial slots 64 that receive the rear latches 52 of the main connector housing 34. The main body 60 also defines retention shoulder 66 adjacent a rear end of the main body 60. Catches 68 of the rear latches 52 of the main connector housing 34 engage the retention shoulder 66 to provide the snap-fit connection between the main connector housing 34 and the mounting block 30.

As shown at FIG. 3, the mounting block 30 includes a two-piece construction including an upper piece 30A and a lower piece 30B that can be fastened together by a snap-fit connection provided by latches 70. As indicated above, axially spaced-apart ribs can be provided within the main body 60 to provide the interlock between the main body 60 and the strain relief sleeve 32. By positioning the top and bottom pieces 30A, 30B of the mounting block 30 so that the axial ribs align with the circumferential grooves 56 of the strain relief sleeve 32, and then snapping the top and bottom pieces 30A, 30B together around the strain relief sleeve 32, the mounting block 30 and the strain relief 32 are effectively interlocked together.

The top and bottom pieces 30A, 30B of the mounting block 30 can include mating pins 74 and openings 76 provided at the front extension 62 at the interface between the top and bottom pieces 30A, 30B (see FIG. 5). The mating pins 74 and openings 76 assist in maintaining alignment between the top and bottom pieces 30A, 30B of the mounting block 30.

The ferrule 24, the ferrule hub 26, the spring 28, and the strain relief sleeve 32 can form a first sub-assembly 80 (see FIG. 4) of the fiber optic connector 20. In certain examples, the first sub-assembly can be factory installed on the optical fiber 22. Similarly, the front end face 46 of the optical fiber 22 can be factory processed (e.g., polished). In certain examples, the strain relief sleeve 32 and the spring 28 can be slid over the optical fiber 22 in the factory. Thereafter, the ferrule 24 and the ferrule hub 26 can be mounted at the end of the optical fiber 22 and the end faces of the optical fiber 22 and the ferrule 24 can be processed in a factory setting.

In certain examples, the ferrule 24 can be mounted in the ferrule hub 26 such that a rotational position of a core offset of the optical fiber 22 relative to the ferrule 24 is set at predetermined rotational position relative to the ferrule hub 26. This core offset provides tuning of the connector. The term "core offset" refers to a direction in which the core is offset from being perfectly concentric with the ferrule 24. In certain examples, the end face of the ferrule 24 can be polished at an angle, and the ferrule 24 can be mounted in the ferrule hub 26 such that the angle can be set at a desired rotational orientation relative to the ferrule hub 26 in the factory. Providing a keyed relationship between the ferrule hub 26 and the main connector housing 34, combined with establishing a predetermined rotational relationship between the ferrule hub 26 and the angle or core concentricity of the ferrule end face 44, enables the angle of the end face or the core concentricity to be set at a predetermined rotational orientation relative to the main connector housing 34.

Figure 14:
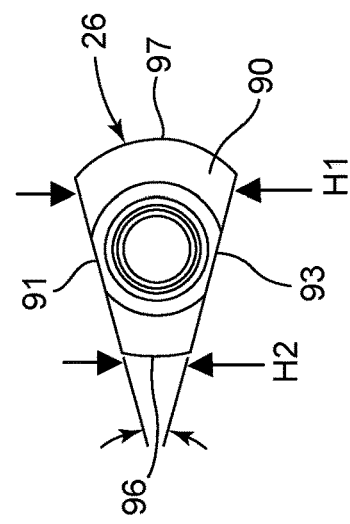
FIG. 14 is a front end view of the ferrule hub of FIG. 11.
Figure 13:
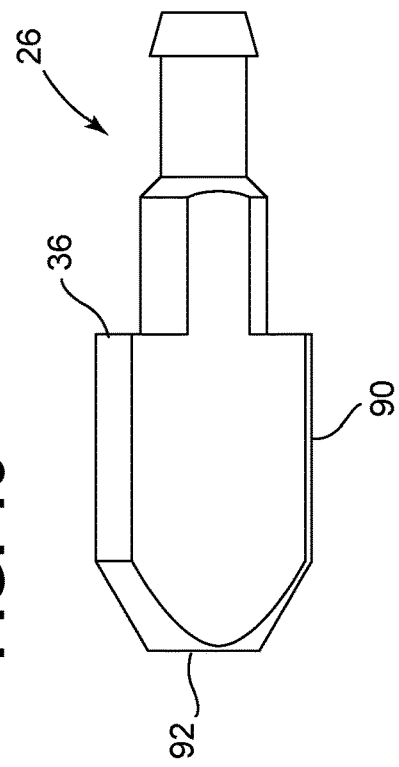
FIG. 13 is a top view of the ferrule hub of FIG. 11.
Figure 12:
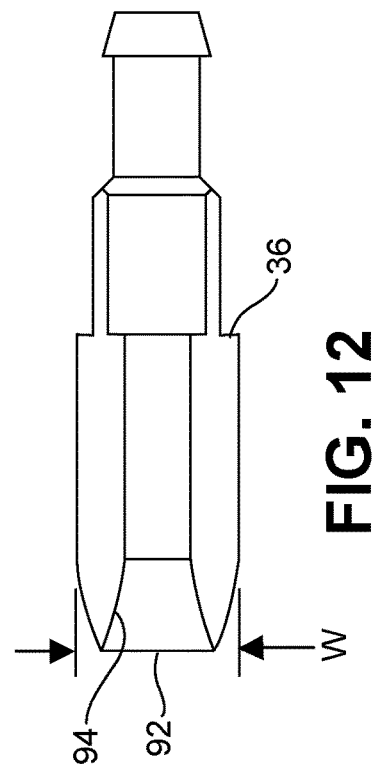
FIG. 12 is a side view of the ferrule hub of FIG. 11.

Referring to FIGS. 7, 8, and 11-14, the ferrule hub 26 defines a central opening for receiving the optical fiber 22. The ferrule hub 26 includes a main body 90 having a front end 92 defining a receptacle 94 for receiving a rear end of the ferrule 24. As shown at FIG. 14, the main body 90 has opposite top and bottom major sides 91, 93 that are angled relative to one another. As shown at FIG. 14, the top and bottom major sides 91, 93 extend across a width W of the main body 90. The width W extends between left and right sides 96, 97 of the main body 90. The right side 97 has a height H1 that is larger than a height H2 defined at the left side 96 of the main body 90. This difference in height is provided by the taper angle between the top and bottom major sides 91, 93. It will be appreciated that the shape of the main body 90 compliments a corresponding shape of a pocket 100 defined within the interior of the main connector housing 34. The complimentary shape between the main body 90 and the pocket 100 (see FIG. 15) ensures that the ferrule hub 26 can be inserted into the main connector housing 34 in only one rotational position. The single rotational position is dictated by the angled top and bottom surfaces 91, 93 and corresponding angled top and bottom surfaces 101, 103 of the pocket 100 within the main connector housing 34.

Referring back to FIGS. 1 and 3, the mounting block 30 and the main connector housing 34 can form a second sub-assembly 110. In certain examples, the second sub assembly 110 can be installed over the first sub-assembly 80 in the field (see FIG. 3). For example, the first sub-assembly 80 can be factory installed on the optical fiber 22. The optical fiber 22 with the first sub-assembly 80 installed thereon can then be delivered to a field location. One example field location is a multi-dwelling unit or other building. The optical fiber 22 with the first sub-assembly 80 mounted thereon can then be installed at the field location. For example, the optical fiber 22 with the first sub-assembly 80 mounted thereon can be routed along one or more routing paths that may extend through structures, such as ducts, risers, plenums, or other passages. The relatively small cross-sectional profile of the first sub-assembly 80 allows the optical fiber 22 with the first sub-assembly 80 mounted thereon to be easily routed along the desired routing path even in situations where the optical fiber 22 is routed through ducts having relatively small internal passages. The small cross-sectional profile also allows multiple optical fibers 22 to be incorporated into a carrier (e.g., a sleeve, tube, pulling sock, jacket, etc.) having a small form factor.

Figure 16:
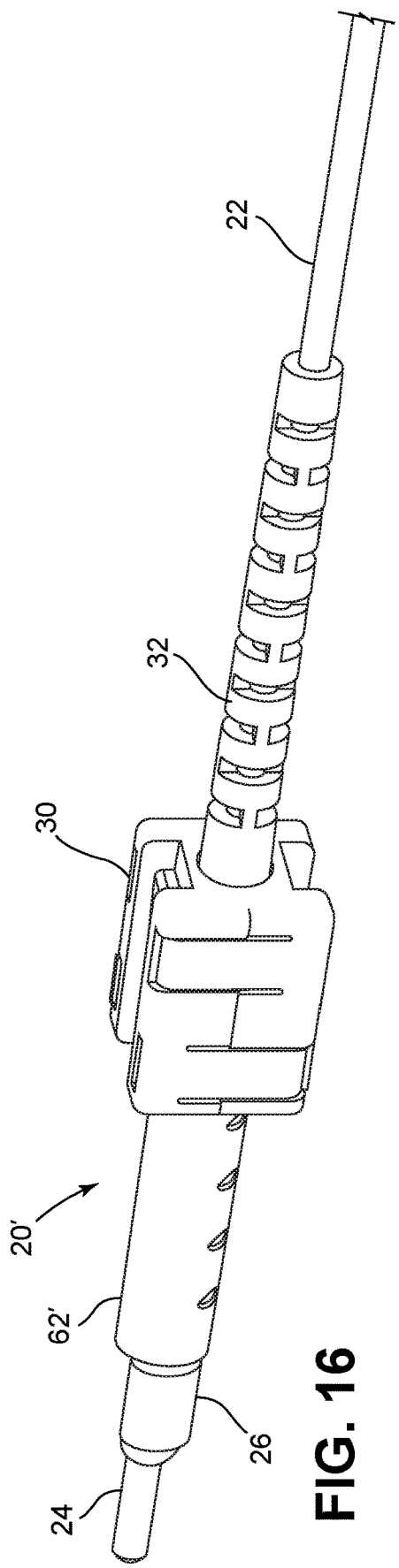
FIG. 16 shows a portion of a springless fiber optic connector in accordance with the principles of the present disclosure.

When the end of the optical fiber 22 with the first sub-assembly 80 mounted thereon has been routed to a desired position at the field location, the mounting block 30 can be snapped over the strain relief sleeve 32; and the ferrule 22, the ferrule hub 26, and the spring 28 can be inserted into the backside of the main connector housing 34. The main connector housing 34 is then latched to the mounting block 30 and the fiber optic connector 20 is fully assembled. Thereafter, the fiber optic connector 20 can be used in the same way as a standard type of connector. For certain applications, it will be appreciated that the spring 28 may be optional. In this regard, FIG. 16 shows an alternative connector 20' where the spring 28 has been eliminated and a front extension 62' of the mounting block 30 has been extended to fill the space that would typically be occupied by the spring 28.

What is claimed is:

1. A connectorized cable assembly comprising:
a first sub-assembly including an optical fiber, the optical fiber carrying a strain relief sleeve having a central opening through which the strain relief sleeve receives the optical fiber along an axial direction of the optical fiber, the first sub-assembly also including a ferrule carrying a terminated end of the optical fiber so that the terminated end of the optical fiber is accessible from an end face of the ferrule, the first sub-assembly also including a spring; and
a second sub-assembly that can be installed at least partially over the first sub-assembly, the second sub-assembly including a rear housing and a front housing, the rear housing including at least a first body having an axially extending open channel configured to receive at least a portion of the first sub-assembly, wherein the first body is mounted over the at least a portion of the first sub-assembly in a radial direction relative to the optical fiber, and the front housing being configured to attach to the rear housing by sliding the front housing over at least a portion of the first sub-assembly along the axial direction to mount at least partially over the ferrule, wherein the strain relief sleeve couples to the rear housing.

2. The connectorized cable assembly of claim 1, wherein the rear housing is radially mounted over the strain relief sleeve.

3. The connectorized cable assembly of claim 1, wherein the rear housing further includes a second body that couples to the first body.

4. The connectorized cable assembly of claim 3, wherein the first and second bodies snap-fit together.

5. The connectorized cable assembly of claim 1, wherein the front housing is axially attached to the rear housing.

6. The connectorized cable assembly of claim 1, wherein the first body includes a main body and a front extension that extends forwardly of the main body to a front axial end of the rear housing.

7. The connectorized cable assembly of claim 6, wherein the main body engages the strain relief sleeve.

8. The connectorized cable assembly of claim 6, wherein the front housing engages the main body when the front housing is attached to the rear housing.

9. The connectorized cable assembly of claim 1, wherein the rear housing defines a spring stop for the spring carried by the first sub-assembly.

10. The connectorized cable assembly of claim 6, wherein at least a portion of the rear housing is generally rectangular.

11. The connectorized cable assembly of claim 6, wherein the front extension is smaller than the main body.

12. The connectorized cable assembly of claim 1, wherein at least a portion of the strain relief sleeve has a tapered construction.

13. The connectorized cable assembly of claim 1, wherein the first sub-assembly includes a ferrule hub that is keyed to at least one of the front housing and the rear housing.

14. The connectorized cable assembly of claim 13, wherein the ferrule hub is keyed to insert into the front housing in only one rotational orientation.

15. The connectorized cable assembly of claim 13, wherein the ferrule hub has an asymmetric construction.

16. The connectorized cable assembly of claim 1, wherein the front housing defines an LC-type connector housing.

17. The connectorized cable assembly of claim 1, wherein the rear housing is spaced from the ferrule by at least the length of the spring.

18. The connectorized cable assembly of claim 1, wherein the front housing latches to the rear housing.

19. The connectorized cable assembly of claim 18, wherein the front housing includes latch fingers.

20. A connectorized cable assembly:
a ferrule supporting a terminal end of an optical fiber of a cable;
a ferrule hub supporting the ferrule;
a spring disposed at a backside of the ferrule hub;
an axial stop coupled to the cable and spaced from the ferrule hub;
a rear housing including at least a first body having an axially extending open channel, the first body configured to mount radially onto at least the axial stop, wherein the axially extending open channel of the first body is configured to at least partially engage the axial stop such that rearward axial movement of the rear housing relative to the cable is prevented; and
a front housing connected to the rear housing and mounted at least partially over the ferrule, wherein the front housing is configured to axially slide over the terminal end of the optical fiber to connect to the rear housing.

21. The connectorized cable assembly of claim 20, wherein the axial stop is formed from a boot.

22. The connectorized cable assembly of claim 20, wherein the rear housing is of two-piece construction and includes a second body.

23. The connectorized cable assembly of claim 20, wherein the rear housing defines a spring stop and the spring is captured between the backside of the ferrule hub and the spring stop when the connectorized cable assembly is assembled.

24. The connectorized cable assembly of claim 20, wherein the front housing is snap-fit to the rear housing.

25. The connectorized cable assembly of claim 24, wherein the front housing includes latches configured to snap-fit to the rear housing.

26. The connectorized cable assembly of claim 20, wherein the ferrule hub is keyed to at least one of the front housing and the rear housing for rotational orientation during assembly of the connectorized cable assembly.

27. The connectorized cable assembly of claim 26, wherein the ferrule hub is asymmetric in at least one direction.

* * * * *